(12) United States Patent
Mamun et al.

(10) Patent No.: US 11,156,555 B2
(45) Date of Patent: Oct. 26, 2021

(54) OPTICAL FIBRE BASED MICROPROBE

(71) Applicant: Swinburne University of Technology, Hawthorn (AU)

(72) Inventors: Md Abdullah Al Mamun, Dacca (BD); Paul Randall Stoddart, Warburton (AU); Anita Mahadevan-Jansen, Nashville, TN (US); Nerida Anne Cole, Auburn (AU)

(73) Assignees: Swinburne University of Technology, Hawthorn (AU); Vanderbilt University, Nashville, TN (US)

( * ) Notice: Subject to any disclaimer, the term of this patent is extended or adjusted under 35 U.S.C. 154(b) by 0 days.

(21) Appl. No.: 16/964,569

(22) PCT Filed: Jan. 25, 2019

(86) PCT No.: PCT/AU2019/050056
§ 371 (c)(1),
(2) Date: Jul. 23, 2020

(87) PCT Pub. No.: WO2019/144195
PCT Pub. Date: Aug. 1, 2019

(65) Prior Publication Data
US 2021/0041366 A1    Feb. 11, 2021

(30) Foreign Application Priority Data

Jan. 25, 2018   (AU) ............................... 2018900246

(51) Int. Cl.
*G01N 21/65* (2006.01)
*A61B 5/00* (2006.01)

(52) U.S. Cl.
CPC .......... *G01N 21/658* (2013.01); *A61B 5/0075* (2013.01); *G01N 2201/063* (2013.01);
(Continued)

(58) Field of Classification Search
CPC .......... G01N 21/658; G01N 2201/063; G01N 2201/08; A61B 5/0075
See application file for complete search history.

(56) References Cited

U.S. PATENT DOCUMENTS 5,710,626 A   1/1998   O'Rourke et al.
5,963,319 A   10/1999  Jarvis et al.
(Continued)

OTHER PUBLICATIONS

International Search Report and Written Opinion for International Application No. PCT/AU2019/050056, dated Apr. 8, 2019.
(Continued)

*Primary Examiner* — Jamil Ahmed
(74) *Attorney, Agent, or Firm* — Wolf, Greenfield & Sacks, P.C.

(57) ABSTRACT

The present application discloses a spectroscopy probe for a Raman spectroscopy system, and methods for preparing filters for the probe. A method for forming an SERS substrate which can optionally be used with the probe is also described. The spectroscopy probe is formed using a double-clad optical fibre probe tip, the double-clad optical fibre (DCF) having a single mode core, multimode inner cladding, and outer cladding, and a micro-filter fixed to the distal end of the optical fibre probe tip. The micro-filter has a short pass or band pass filter configured to align with the DCF core to filter silica Raman background generated by laser excitation in the single mode core, and a long pass filter configured to suppress Rayleigh scattering from the sample while allowing Raman scattered wavelengths to be transmitted through the inner cladding.

20 Claims, 10 Drawing Sheets

(52) U.S. Cl.
CPC .............. *G01N 2201/06113* (2013.01); *G01N 2201/08* (2013.01)

(56) References Cited

U.S. PATENT DOCUMENTS

| | | |
|---|---|---|
| 8,085,464 B2 | 12/2011 | Gonthier et al. |
| 2015/0216417 A1 | 8/2015 | Huang et al. |
| 2019/0059734 A1* | 2/2019 | Yamada .............. A61B 5/6852 |

OTHER PUBLICATIONS

International Preliminary Report on Patentability for International Application No. PCT/AU2019/050056, dated Apr. 6, 2020.
PCT/AU2019/050056, Apr. 8, 2019, International Search Report and Written Opinion.
PCT/AU2019/050056, Apr. 6, 2020, International Preliminary Report on Patentability.

* cited by examiner

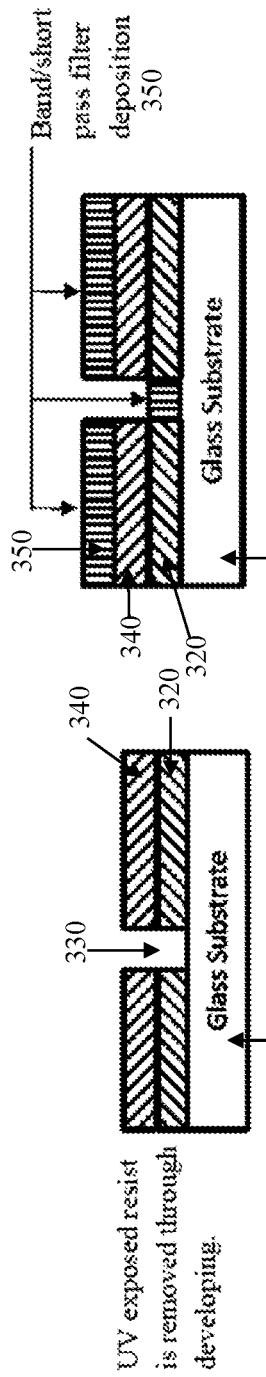
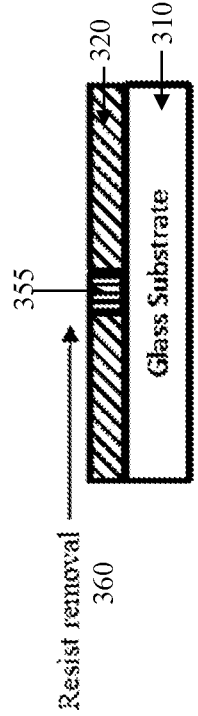
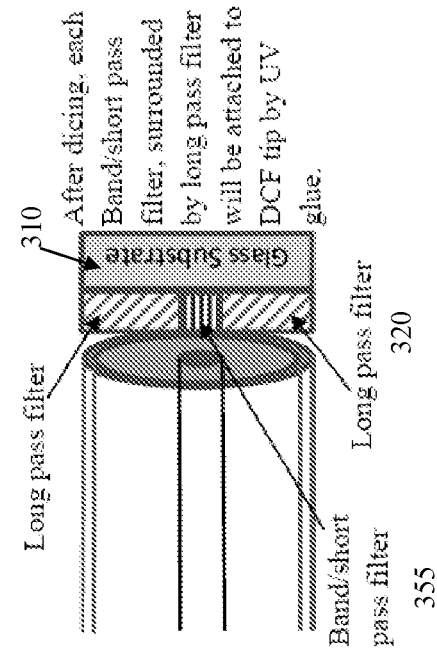
Figure 3e
Figure 3f
Figure 3g
Figure 4

OPTICAL FIBRE BASED MICROPROBE

CROSS REFERENCE OF RELATED APPLICATIONS

This Application is a national stage filing under 35 U.S.C. § 371 of International Patent Application Serial No. PCT/AU2019/050056, filed Jan. 25, 2019, which claims priority to Australian application number 2018900246, filed Jan. 25, 2018. The contents of these applications are incorporated herein by reference in their entirety.

TECHNICAL FIELD

The field of the invention is probes for Raman spectroscopy and surface-enhanced Raman scattering (SERS).

BACKGROUND

Raman spectroscopy is a vibrational scattering process that allows the detection of a wide range of substances, based on their unique spectrum. Surface-enhanced Raman scattering allows more sensitive detection of target substances that are in close contact with certain roughened metal surfaces.

There are two problems that hinder the use of optical fibre probes in chemical sensing applications. The first problem is the silica Raman background generated in both the excitation and collection fibres can dominate the spectrum and swamp the target spectrum. This silica Raman background generated within the fibre occurs primarily in the fingerprinting region of the Raman spectrum and can easily overwhelm the signal from the sample. Filtering is required to suppress this background and improve the output signal to noise ratio.

In current commercially available fibre optic probes for Raman spectroscopy these filters are implemented with the free-space optical components, such as lenses and mirrors, required to couple light into and out of the optical fibre probe. This leads to the second problem in that such free-space optics can be bulky and require precision alignment. Typically adjustment of the free space optics is required for each device during equipment assembly. In use, careful handling is required to avoid compromising the optics alignment. The use of bulky filters to eliminate the silica Raman background and lenses to couple light into and out of the bundle of fibres or fibre can cause optical losses and this hinders the use of fibre SERS probes in some sensing applications e.g. biomedical sensing.

Some Raman probe configurations with probe tip filtering use two or more optical fibres arranged in different configurations with one fibre being used to transmit the excitation light and other fibre for receiving the Raman signals. Myrick M L, Angel S M (1990) Appl Spectrosc 44:565-570 disclose that filtering can be achieved by breaking the fibre bundle near the sampling end, separating the excitation and collection fibres, and then butting the fibres up against appropriate dielectric filters. A problem with this arrangement is that coupling is relatively inefficient owing to the thickness of the filters. Graded-index rod lenses can be used at the end of each fibre to collimate the light. This arrangement can be lossy and bulky, limiting its suitability for some applications, in particular in medical diagnostics.

Komachi Y, Sato H, Matsuura Y, Miyagi M, Tashiro H (2005) Opt Lett 31:1911-1913, discloses a probe configuration comprising a bundle of optical fibres surrounded by metal sheathes and having probe tip filtering. One fibre (for example central to the bundle) is separately sheathed for transmitting excitation light, isolated from the remaining fibres in the bundle. The other fibres, for receiving the Raman signals, are bundled in a separate sheath surrounding or adjacent to the sheathed excitation fibre. Individually machined filters of submillimetre dimensions are positioned at the ends of the fibre, inserted into the sheaths, to provide a band pass filter for the excitation filter and a long pass filter for the Raman signal fibres. The excitation fibre may be separated from the bundle at the proximal end for connection to the excitation laser and the remainder of the bundle positioned for transmission of Raman signals to a detector via free space optics. This structure provides the smallest known distal Raman probe, with distal end filtering, having a diameter of around 600 µm. However, the probe is rigid due to the metal sheathing and both probe and filter manufacture are complex and expensive.

Although these probe configurations allow small probes, the structures required for supporting the filtering and bundling of the fibres restrict their application, particularly in medical diagnostics. Fabrication of these probes is also complicated. Free space optics are also still required for transmission of Raman signals from the fibre bundles to the detector.

There is a need for alternative probes.

SUMMARY OF THE INVENTION

A first aspect provides a spectroscopy probe for a Raman spectroscopy system, the probe comprising:
- a double-clad optical fibre probe tip, the double-clad optical fibre (DCF) having a single mode core, multimode inner cladding, and outer cladding; and
- a micro-filter fixed to the distal end of the optical fibre probe tip,
  the micro-filter comprising:
    a short pass or band pass filter configured to align with the DCF core to filter silica Raman background generated by laser excitation in the single mode core, and
    a long pass filter configured to suppress Rayleigh scattering from the sample while allowing Raman scattered wavelengths to be transmitted through the inner cladding.

In an embodiment the micro-filter is substantially planar and wherein the long pass filter surrounds the short pass or band pass filter aligned substantially in the same plane and the outer diameter of the filter at least matches the diameter of the inner cladding of the double-clad optical fibre.

In some embodiments of the probe tip, the micro-filter further comprises a surface-enhanced Raman scattering (SERS) substrate. The SERS substrate can be applied using a photo chemical deposition technique. In an embodiment a SERS substrate is applied by:
- inserting the probe tip into a photochemical growth solution; and
- applying laser irradiation via the DCF core for a period of time to stimulate photochemical deposition on the probe tip from the growth solution.

In an embodiment of the spectroscopy probe the micro-filter is attached directly to the end of the optical fibre using UV light curable adhesive.

Some embodiments of the spectroscopy probe further comprise a double-clad optical fibre coupler configured to couple a double-clad optical fibre and a multimode fibre, wherein a distal end of the double-clad optical fibre forms the probe tip and a proximal end of the double-clad optical fibre is configured for connection to an excitation output of the Raman spectroscopy system, to in use convey excitation wavelengths to the probe tip via the core of the double-clad optical fibre; and a proximal end of the multimode fibre is configured for connection to a detector input of the Raman spectroscopy system, such that Raman scattered wavelengths transmitted through the inner cladding of the double-clad optical fibre in response to excitation are coupled to the multimode fibre for reception by the detector.

Another aspect provides a method of fabricating a Raman spectroscopy micro-filter for a Raman spectroscopy probe. In one embodiment the method comprises the steps of:
  depositing on an optically transparent substrate a thin film of material having long pass filter properties, to provide a long pass filter layer;
  removing a section of the long pass filter layer to leave a hole in the long pass filter layer to align with an optical fibre inner core;
  applying a layer of resist coating, whereby the resist coating fills the hole and provides a layer over the long pass filter layer, the resist coating being removable through developing after exposure to UV light;
  illuminating the glass substrate with UV light whereby the long pass filter layer blocks the UV light and the resist filling and above the hole is exposed to UV radiation;
  developing to remove the UV exposed resist, to leave empty the hole extending through the long pass filter layer and resist layer;
  depositing a thin film of material having short or band pass properties to provide at least a layer of short or band pass filter material on the substrate inside the hole; and
  removing the resist layer and any band pass filter material on top of the resist layer to provide a substantially planar filter surface, the resulting micro-filter comprising a filter layer having a short or band pass filter surrounded by a long pass filter supported on a substrate.

In an alternative embodiment a method of fabricating a Raman spectroscopy micro-filter for a Raman spectroscopy probe comprises the steps of:
  depositing on a first side of an optically transparent substrate a thin film of material having long pass filter properties, to provide a long pass filter layer;
  depositing a thin film of material having short pass filter properties, on a second side of the substrate to provide a short pass filter layer;
  removing a ring-shaped section of the short or band pass filter layer to leave a central circular portion and an annular outer ring portion;
  removing a section of the long pass filter layer to leave a hole in the long pass filter layer aligned with the central circular portion of the short pas filter; and attaching a further substrate to the long pass filter layer, to provide a resulting micro-filter comprising annular long pass and short pass filters, with a short or band pass filter surrounded by a long pass filter supported on a substrate.

In embodiments of either method the step of removing a section of the long pass filter layer can comprise any one or more of: drilling, laser drilling, micromachining or etching.

In an embodiment the hole diameter is around 4-15 µm.

In some embodiments the method is used to produce a plurality of micro-filters on one substrate and the step of removing a section of the long pass filter layer comprises removing a plurality of sections of the long pass filter layer, to provide one hole for each micro-filter. In this embodiment the method further comprises the further step of separating the individual filters.

In some embodiments the substrate is formed of any one or combination of, glass or fused silica.

The method can further comprise the step of attaching the micro-filter to a double-clad optical fibre probe tip, with the short pass filter aligned with the optical fibre core. For example, the micro-filter can be attached to the probe tip using UV cured adhesive.

An embodiment of the method further comprises applying a surface enhanced Raman scattering (SERS) substrate to the micro-filter at the probe tip.

In some embodiments the SERS substrate is formed on top of a target analyte capture layer. In such embodiments target analyte capture layer can be formed by:
  coating the probe tip surface with a layer of streptavidin;
  providing biotinylated analyte to the streptavidin substrate; and
  incubating to partition the biotinylated analyte onto the surface by biotin-streptavidin interaction to form the target analyte capture layer.

In some embodiments applying a SERS substrate comprises the steps of:
  inserting the probe tip into a photochemical growth solution; and
  applying laser irradiation via the DCF core for a period of time to stimulate photochemical deposition on the probe tip from the growth solution.

In an embodiment the photochemical growth solution is an aqueous solution of silver nitrate and trisodium citrate, for deposition of silver nanoparticles in response to irradiation.

BRIEF DESCRIPTION OF THE DRAWINGS

An embodiment, incorporating all aspects of the invention, will now be described by way of example only with reference to the accompanying drawings in which:

FIGS. 3a to 3g illustrate steps of a process for manufacturing an embodiment of a micro-filter;

FIG. 4 illustrates fixing the micro-filter to a probe tip;

DETAILED DESCRIPTION

Figure 1:
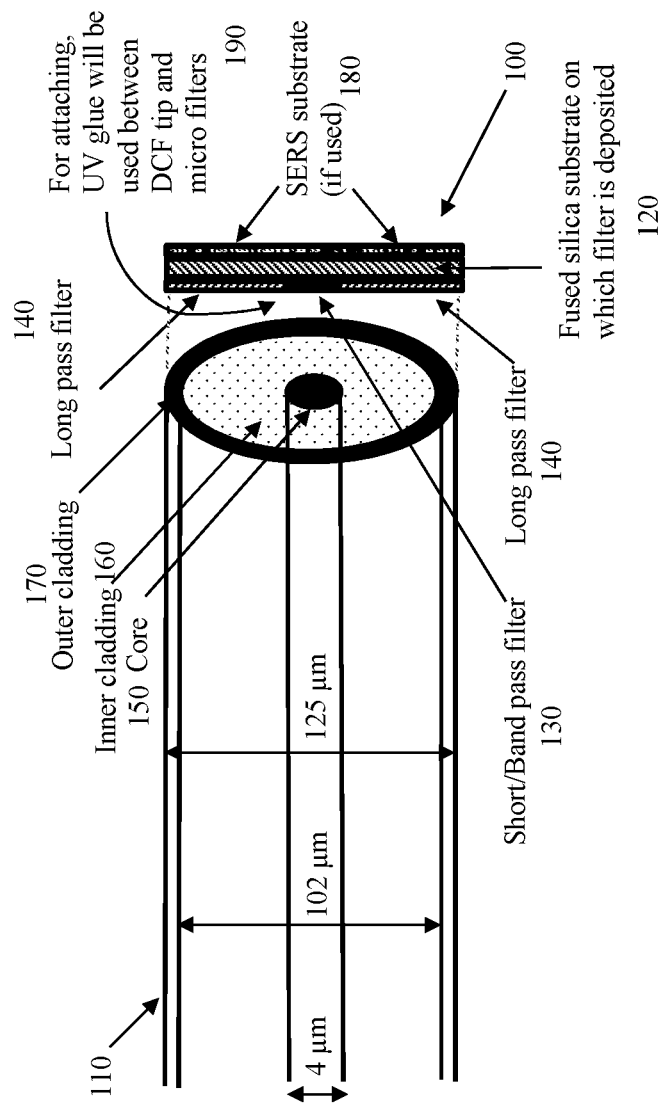
FIG. 1 shows an enlarged view of a spectroscopy probe tip with filtering assemblies.

This description relates to an optical fibre-based probe for Raman spectroscopy and surface-enhanced Raman scattering (SERS). Embodiments provide a microprobe featuring an integrated micro-filtering arrangement, and a method for manufacturing the micro-filter for the probe.

Two issues in the development of high performance fibre optic SERS probes is the reduction of optical fibre Raman background and integration of optical components. To solve these issues, an integrated micro-filtering mechanism has been devised, based on double-clad optical fibre (DCF), also referred to as dual-clad optical fibre. The double-clad optical fibre comprises a single mode core surrounded by a multi-mode inner cladding and surrounded by outer cladding, with each of the core, inner and outer cladding having different (progressively lower) refractive indexes.

Probe embodiments encompass a probe tip comprising a double-clad optical fibre (DCF) and a micro-filter fixed to the distal end of the optical fibre.

Although it may be tempting to simplify the probe by using a single-fibre "optrode" to carry the excitation and scattered light, it has been shown (by Chong C K, Shen C B, Fong Y, Zhu J X, Yan F X, Brush S, Mann C K, Vickers T J (1992) Vib Spectrosc 3:35-45) that bidirectional fibre designs have no practical advantage for normal Raman spectroscopy (NRS), as this geometry yields the largest silica Raman background of all the unfiltered probes. Although the efficiency of this design might be expected to be better than that of N-around-1 probes owing to the complete overlap between the excitation and collection light cones, beam splitter losses more than offset these gains when the excitation light and the scattered light are separated at the spectrometer.

The use of double-clad fibre aims to resolve these limitations of single fibre optrodes, as the excitation and collection pathways are now largely separated. The combination of single mode delivery and multi-mode collection is largely analogous to the N-around-1 multi-fibre designs (e.g. U.S. Pat. No. 6,208,887B1), but offers significant advantages. Examples of advantages can include: a robust, integrated single fibre structure; availability of efficient couplers to separate the excitation and collection pathways; no need to improve the collection efficiency by controlling the fibre separation, angling the fibres or beveling the fibre end faces; and/or potential for integrated filtering.

A first embodiment provides a spectroscopy probe for a Raman spectroscopy system, the probe having a double-clad optical fibre probe tip with a micro-filter fixed to the distal end of the optical fibre probe tip. The micro-filter comprises a short pass or band pass filter configured to align with the double-clad optical fibre core, and a long pass filter. The short pass or band pass filter functions to filter silica Raman background generated by laser excitation in the single mode core. The long pass filter functions to suppress Rayleigh scattering from the sample while allowing Raman scattered wavelengths to be transmitted through the inner cladding.

In this embodiment the micro-filter is substantially planar with the long pass filter adjacent the short pass or band pass filter and aligned in the same plane to coincide with the multimodal inner cladding of the DCF. The long pass filter surrounds the short or band pass filter. The outer diameter of the filter at least matches the diameter of the inner cladding of the double-clad optical fibre.

The distal end of the probe tip is the end of the probe which is brought proximate the sample for testing using Raman spectroscopy. In embodiments of the present invention this distal tip carries the micro-filter. The micro-filter can have the same diameter as the optical fibre. This can enable extremely small diameter and flexible probes.

FIG. 1 represents an example of the micro-filter 100 configured for attachment to a double-clad optical fibre probe tip 110. The micro-filter 100 comprises a substrate 120 on which the filter is deposited, for example the substrate can be formed of glass or fused silica substrate. The substrate may be formed of other materials which provide sufficient mechanical support for the filter films, are optically flat and are transparent to the wavelengths required for Raman Spectroscopy.

The filter structure is a substantially planar composite filter supported on the substrate 120, comprising a short or band pass filter portion 130 substantially aligned with the core 150 of the optical fibre probe tip 110, surrounded by a long pass filter 140 to substantially match the outer diameter of the optical fibre tip 110. The band pass filter may be a substantially circular disc shape having a diameter at least matching that of the probe tip core, for example around 4-10 µm. The diameter of the band pass filter may be marginally larger than the core. For example, this can be advantageous to avoid 'edge effects,' where the two filters merge and performance is diminished, being incident with the DCF core. This can also be advantageous for alignment tolerance.

This short or band pass filter is annularly surrounded by the long pass filter to form a larger disc at least matching the diameter of the inner cladding 160 of the optical fibre, for example 102 µm. The long pass filter 140 outer diameter may match that of the outer cladding 170 of the optical fibre tip for ease of alignment when fixing the micro-filter to the probe tip 110. It should be appreciated that the filter structure is rather like a planar long pass filter "donut" with the hole filled in by the band pass or short pass filter. The short pass or band pass filter removes silica Raman background generated by the laser excitation in the single mode core, while the long pass filter blocks the relatively strong Rayleigh scattering from the sample, but allows the Raman scattered wavelengths to be efficiently collected by the multimode inner cladding of the DCF. An example of a fabrication method for such a filter is described in more detail below.

The micro-filter can be attached to the probe tip 110 using adhesive. For example, UV activated adhesive otherwise referred to as UV glue. Such adhesives can be advantageous as the adhesive is cured by UV or visible light so the micro-filter alignment can be adjusted during fixing before the glue is "cured" to permanently attach the micro-filter to the probe tip. Preferred glues are also transparent at the required wavelengths for Raman spectroscopy, exhibit low fluorescence background and have similar refractive index to the optical fibre to reduce reflection losses at the interface. It should be appreciated that a variety of different 'grades' of optical adhesives exist that have different refractive indices, reduced fluorescence, transparency windows, etc. The choice of adhesive can depend on requirements of the particular embodiment.

In some embodiments the micro-filter further comprises a surface-enhanced Raman scattering (SERS) substrate. In some embodiments this SERS substrate can be formed on the probe tip after attaching the micro-filter. Some known materials for SERS substrates include gold and silver. Materials which are favoured for SERS substrates are characterised by high SERS enhancements at common laser wavelengths in the visible and near infrared; roughness on a nanometer scale to promote the localized surface plasmon resonance; and discontinuous films can be preferred to facilitate transmission of SERS through the film. The SERS substrate is discussed in further detail below.

In some embodiments the micro-filter may be manufactured with a SERS substrate included. Alternatively the SERS substrate may be applied to the filter after probe manufacture.

SERS allows highly sensitive detection of analytes that are able to adsorb on the metal surface. It should be appreciated that not all applications require an SERS substrate. Probes with integrated micro-filters may be supplied and a SERS substrate applied to the micro-filter on the probe tip as a separate, later, action if such a substrate is required for a given application.

The micro-filter is fixed to the tip of the optical fibre SERS probe, providing (a) filtering to suppress silica Raman background generated by the laser excitation in the single mode core of the DCF, and (b) efficient collection of Raman or SERS signal in the inner cladding of the DCF while suppressing Rayleigh scattered light from the sample. Suppressing Rayleigh scattered light is desirable because the Rayleigh scattered laser light can generate additional silica Raman background in the fibre. This may have a similar in intensity to the background generated by the laser beam in the inner core, as that background is also Rayleigh scattered back into the collection pathway. Suppressing Rayleigh scattered light can improve the output signal to noise ratio.

An embodiment of a spectroscopy probe, incorporating the micro-filter integrated probe tip as described above, can utilise a double-clad optical fibre coupler to enable the light source input and spectroscopy output to be received at different ports of a Raman spectroscope.

Figure 2:
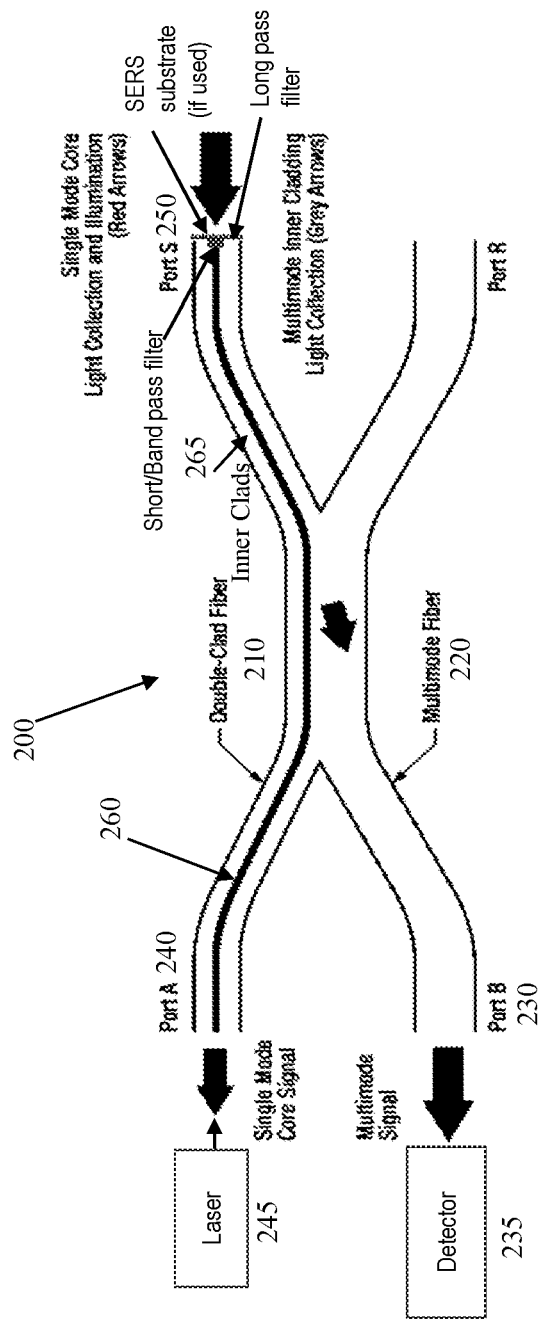
FIG. 2 is a diagrammatic representation of a SERS microprobe with double-clad optical fibre (DCF) coupler and integrated filtering mechanism at Port S.

The concept of using the DCF coupler is shown in FIG. 2, the DCF coupler 200 combines a double-clad fibre 210 having a single mode core surrounded by a multimode inner cladding and an outer cladding, with a multimode fibre 220. The use of a DCF coupler allows the collection port 230 to be separated from the excitation port 240. A spectroscope typically has two ports, a first port for providing laser excitation 245, and a second port for receiving the Raman response signals at a detector 235. In this example the first port is connected to the DCF coupler port A 240 for transmission of laser excitation through the single mode core 260 of the DCF 210 to the probe tip 250. The Raman response signal for the sample is transmitted through the multimode inner cladding of the DCF from the probe tip 250 and coupled to the multimode fibre 220 for transmission to the multimode port B 230 to the Raman spectroscopy detector 235.

This arrangement has an advantage of eliminating the need for discrete optics for separating excitation and collection beam paths. The combination of single mode delivery and multi-mode collection is similar in concept to an N-around-1 multi-fibre designs (for example as shown U.S. Pat. No. 6,208,887). However, the alternative structure using the DCF and DCF couplers provides multiple advantages including but not limited to at least: a robust, integrated single fibre structure; availability of efficient couplers to separate the excitation and collection pathways; no need to improve the collection efficiency by controlling the fibre separation, angling the fibres or beveling the fibre end faces; and/or potential for integrated filtering.

The use of integrated filtering potentially reduces the diameter of the probe 250 (Port S) down to ~125 μm or less (i.e. the outer diameter of the fibre itself). At the time of writing this specification, this would be the smallest diameter of a Raman/SERS probe with an integrated filtering mechanism reported.

To enable manufacture of this probe configuration, methods for minimising the filters, to size for application to the end of an optical fibre, have been developed applying chip-based manufacturing techniques. FIGS. 3a to 3g illustrate a sequence of manufacturing steps to achieve the micro-filter structure.

Figure 3A:
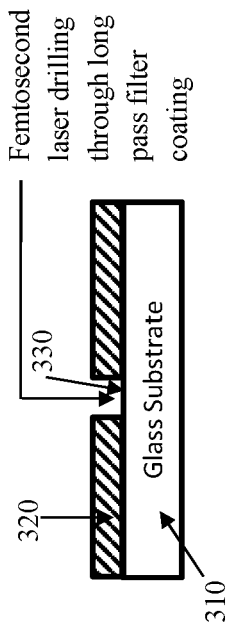

In a first step, as illustrated in FIG. 3a, a long pass filter layer 320 is deposited on a glass substrate 310. The long pass filter layer 320 can be formed by depositing on a glass substrate a thin film of material having long pass filter properties. The long pass filter may be formed using multiple thin film layers in some embodiments.

Figure 3B:
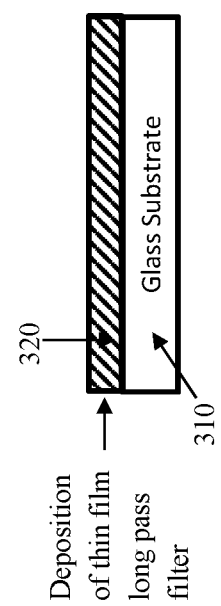

In a second step, as illustrated in FIG. 3b, a section of the long pass filter layer 320 is removed to leave a hole 330 in the long pass filter layer to align with an optical fibre inner core. In an embodiment this removal of the long pass filter layer is achieved using micromachining techniques, for example by femtosecond pulsed laser drilling through the long pass filter coating. Other techniques such as etching may also be used in alternative embodiments. The hole 330 is configured to align with an optical fibre core, so in an embodiment the diameter of the hole is around 4 μm to at least match the core diameter. It should be appreciated that the hole 330 diameter can be substantially matched to the core diameter for a chosen DCF, for example 3-6 μm. The hole may also be slightly larger than the core diameter, for example 5-15 μm to provide a larger alignment tolerance.

The hole would typically be a bit larger than the core, because (a) the single mode optical field extends slightly beyond the core, (b) the filter performance is likely to be degraded at the edges of the filter, and (c) thin film deposition into a deep hole (in terms of aspect ratio) may be disrupted and cause the filter performance to be sub-optimal. For an embodiment it is estimated that a diameter of about 10 μm will be appropriate for a DCF with a 4 μm core. It should be appreciated that this hole (short or band pass filter) diameter still represents a small fraction of the inner cladding area. So signal collection efficiency will not be significantly compromised, for example a circle of diameter 10 micron versus a circle of diameter 100 micron is just 1% of the area.

Figure 3C:
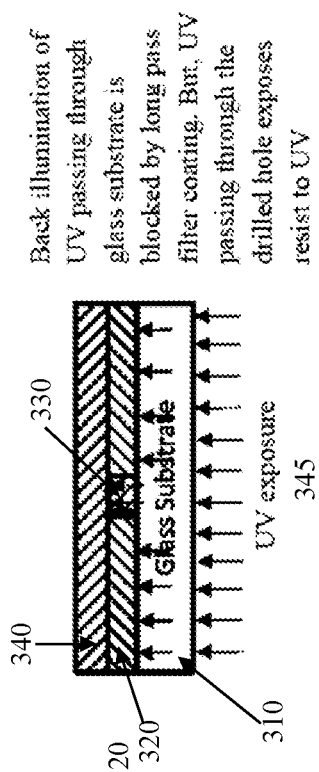

In a third step, as illustrated in FIG. 3c, a layer of resist coating is applied. The resist coating 340 fills the hole 330 and provides a layer over the long pass filter layer 320. In this embodiment the resist coating is of a material that is removable through developing after exposure to UV light. Alternative embodiments may use different resist materials. For example, another class of resist is fixed by exposure to UV, some resists can be exposed by electron beams. UV positive or negative resist material can be preferred in embodiments of this method, to take advantage of the deposited filter properties for masking regions of the resist layer.

Figure 3D:
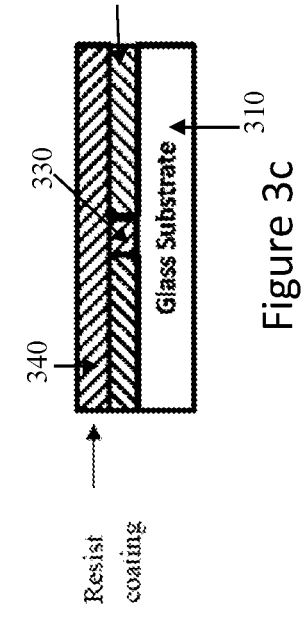

In the fourth step, illustrated in FIG. 3d, the substrate is illuminated using UV light (or other radiation based on the choice of resist coating). During this back illumination the long pass filter layer blocks the UV light and the resist filling and above the hole is exposed to UV radiation. The UV light 345 passes through the glass substrate 310, and in the regions where the long pass filter 320 is deposited on the substrate 310 the filter prevents the UV light 345 affecting the resist coating 340. However, in the hole region 330, where the resist coating 340 is not protected by the long pass filter 320, the resist coating is exposed to UV light. This affects the resist coating 340 in this hole region 330 to allow this exposed part of the resist coating to be removed by developing. As shown illustrated in FIG. 3e this fifth step of developing to remove the UV exposed resist, leaves empty the hole 330 extending through the long pass filter layer 320 and resist layer 340.

In a sixth step, as illustrated in FIG. 3f, a thin film of material having short or band pass properties is deposited to provide at least a second filter layer 350 of short or band pass filter material on the glass substrate 310 inside the hole 330. It should be appreciated that in this step the objective is to deposit the second filter material (short or band pass filter) into the hole 330. However, given the very small size of these filters, this embodiment utilises film deposition techniques which will result in at least some of the second filter material being deposited on top of the resist layer.

In the seventh step, as illustrated in FIG. 3g, the resist coating 340 and any short or band pass filter 350 material on top of the resist layer 340 is stripped to provide a substantially planar filter surface, for example, using a solvent to dissolve the resist layer. It should be appreciated that there may be some variation in depth of the respective long pass and short or band pass filters (for example variation of a few microns). The UV glue for attaching the micro-filter to the probe tip can accommodate some variations in surface level. The DCF fibre tip may also have some variation in end profile, for example the core extending out slightly past the inner cladding. In general, it would be expected that the two filters may have slightly different thicknesses, but these can be accommodated, for example a tolerance of a few microns. The resulting micro-filter comprises a substantially planar composite filter 360 having a short or band pass filter 355 surrounded by a long pass filter 320 supported on the substrate 310.

Figure 9:
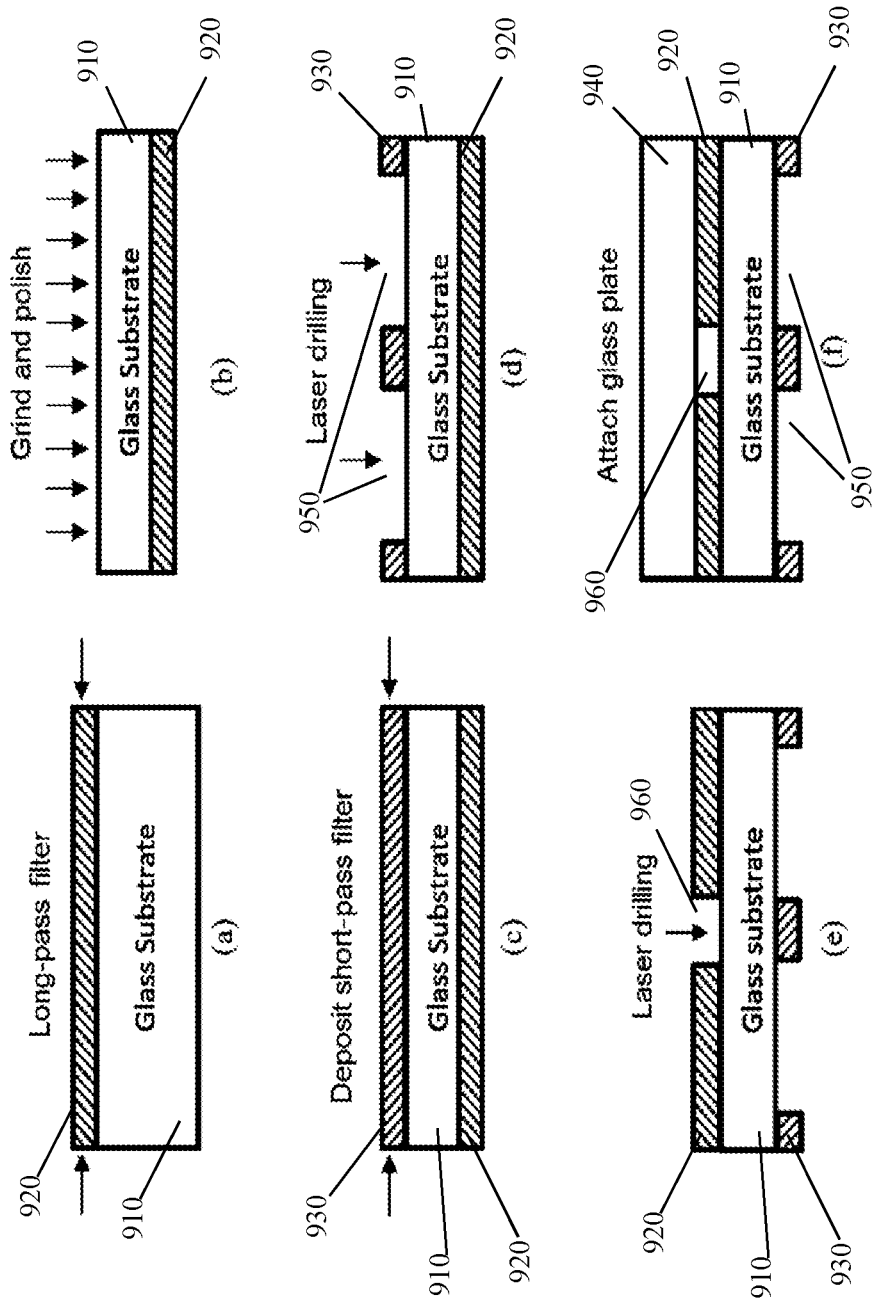
FIG. 9 is a schematic illustration of a sequence of manufacturing steps used to achieve an embodiment of a micro-filter structure on the DCF tip.

An alternative method for producing a filter assembly is illustrated in FIG. 9. This embodiment of the filter assembly is based on a standard long pass filter suitable for removing Rayleigh scattered light and transmitting Raman scattering. In a first step FIG. 9 (a) the long pass filter 920 is formed on a glass plate 910. The long pass filter 920 is back-thinned by grinding to reduce the thickness of the glass plate 910 to less than 1 mm, step (b) FIG. 9. The ground surface is then polished to obtain an optical finish. A short pass filter 930 suitable for transmitting the laser excitation and blocking fibre Raman background is deposited over the back surface of the long pass filter substrate (glass) 910, illustrated in (c) of FIG. 9.

Femtosecond laser drilling is used to remove a donut shaped region 950 from the short pass filter 930 (cross section illustrated in (d) of FIG. 9), where the centre of the donut is matched to the size of the mode field diameter in the DCF core, and the outer diameter of the donut matches the diameter of the inner cladding.

Femtosecond laser drilling is used to remove a circular region 960 from the long pass filter 920, with the circle 960 centre perpendicularly aligned with the centre of the donut 950 in the short pass filter, and the circle 960 diameter matched to the diameter of the beam transmitted through the short pass filter, illustrated in (e) of FIG. 9.

A second glass plate 940 (for example, thickness approximately 1 mm) is glued to the filter plate, illustrated in (f) of FIG. 9, this provides a surface for the SERS substrate. The thickness of the plate 940 allows efficient collection of backscattered Raman light by the inner cladding of the DCF.

Figure 10:
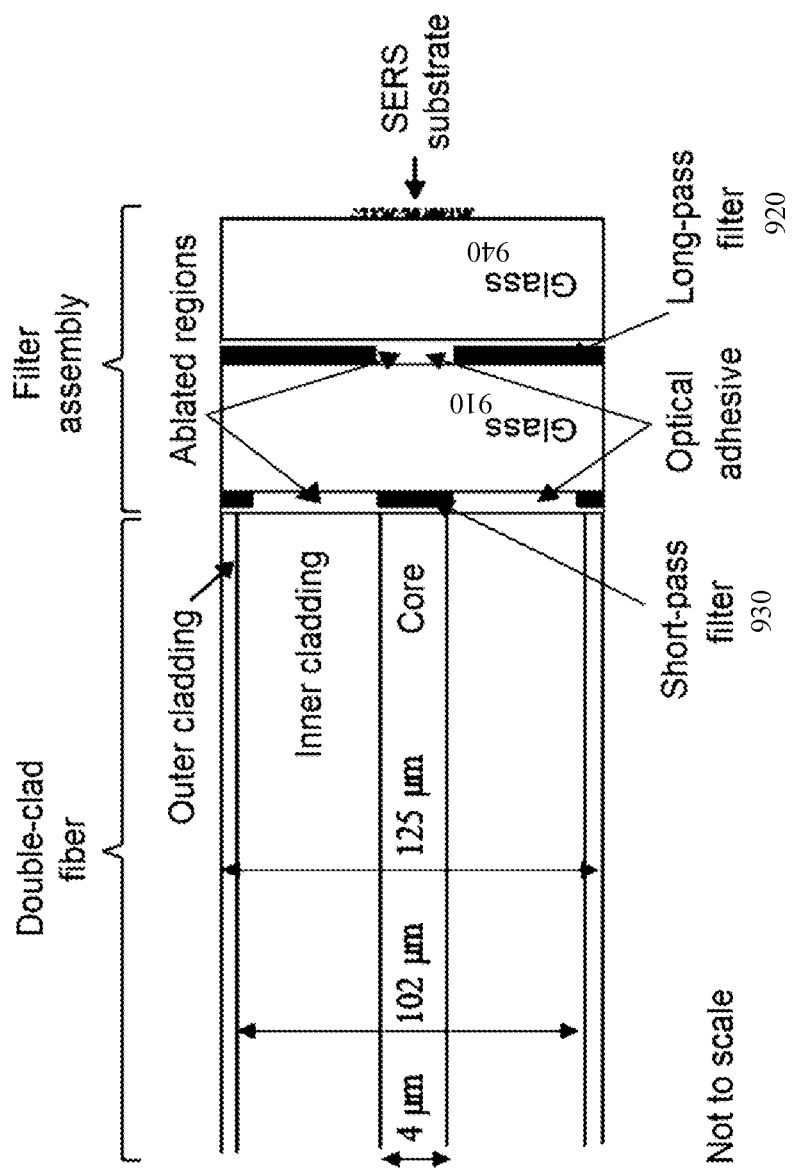
FIG. 10 shows an enlarged view of another embodiment of a double clad fibre (DCF) tip with filtering assembly.

The overall construction of the filter and DCF is shown in FIG. 10, where the filter assembly has been aligned and glued to the cleaved tip of the DCF. FIG. 10 shows an enlarged view of the double clad fibre (DCF) tip with filtering assembly: short pass filter 930 removes silica Raman background generated by the laser excitation in the single mode core and passes the laser excitation through the hole in the long pass filter 920 to generate the SERS spectrum at the outer surface of the assembly. The long pass filter 920 blocks the relatively strong Rayleigh scattering from the sample, but allows the Raman scattered wavelengths to be efficiently collected by the multimode inner cladding of the DCF.

It will be apparent to those skilled in the art that a number of variations are possible on this basic process. For example, lithographic patterning and etching could be used to remove areas of the long- and short-pass filters, instead of the femtosecond laser machining.

The above described process is one method by which the micro-filters are produced. An alternative manufacturing methodology may use a similar process as described above, but starting with the short or band pass filter deposition. Then etch away the band or short pass filter material around the "core" filter regions, for example using a chemical etching process. Then deposit the long pass filter over a suitably patterned resist.

After filter manufacture, each micro-filter can be attached to a DCF tip using an optically transparent adhesive. For example, the adhesive may be UV curable glue. An example of this final step is illustrated in FIG. 4.

The substrate can be any suitable material having suitable optical transparency for the wavelengths required for excitation light and Raman scattering signals. For example, glass, fused silica etc. The substrate thickness can be chosen balancing mechanical requirements to support the filter layers and handling for fixing to the fibre tip. In an embodiment the substrate is a 300 µm thick fused silica substrate. In this embodiment due to film stress the minimum substrate thickness is 300 µm, and thicker substrates may be used. However, differing substrate materials manufacturing technologies may allow thinner substrates to be used.

The filter structure is a substantially planar composite filter, having a short or band pass filter annularly surrounded by a long pass filter. The short or band pass and long pass filters can be composed of continually varying layers of different refractive index. These may be thought of as 'multi-layer' coatings. Any suitable deposition process to achieve the thin planar long pass filter and short or band pass filter may be utilised, and the manufacturing process should not be considered limited to any specific filter deposition process.

The long pass filter (LPF) may be deposited as one or more thin film layers to provide required filter characteristics. For example, the LPF requirement for an embodiment relating to Raman excitation with 514.5 nm laser wavelength may include:
1. Block Rayleigh scattering at 514.5 nm and pass Raman scattering beyond that.
2. Transmission region is 522-627 nm with $T_{abs}$>90%.
3. Rejection region is 500-514.5 nm.
4. Transmission in rejection region is $OD_{abs}$>4.0, $OD_{avg}$>6.0.
5. Filter coating thickness: 4-6 µm.

Note:
Optical Density (OD) is the −log (base 10) of transmittance (T), with T on a zero to unity scale.
Subscript "abs" refers to a limiting (minimum or maximum) value within a specified wavelength range, while "avg" refers to the average value.

The short pass filter (SPF) or band pass filter may be deposited as one or more thin film layers to provide required filter characteristics. The LPF requirement for an embodiment may include:
1. Short pass filter at 514.5 nm.
2. Transmission is at 514.5 nm with $T_{abs}$>90%.

3. Rejection region is 522-627 nm, which corresponds to the Raman shift from 300 to 3500 wavenumber at 514.5 nm.
4. Transmission in rejection region is $OD_{abs}>4.0$, $OD_{avg}>6.0$
5. Filter coating thickness: 4-6 µm.

It should be appreciated that the filter characteristics are dependent on the requirements for Raman spectroscopy. In embodiments of the invention desire to minimising filter thickness needs to be balanced with the spectroscopy performance. Ranges for filter thickness may vary based on filter technology.

In principle filters having a range of wavelengths (mainly dependent on the excitation wavelength) and optical densities could be used in various embodiments. There may be trade-offs between film thickness and optical performance. Thinner films may also have production advantages such as drilling more easily and supporting the second filter deposition with less pronounced 'edge effects' as the vapour enters the hole, but thinner films also have lower optical density which may allow more silica background to pass through.

Figure 5:
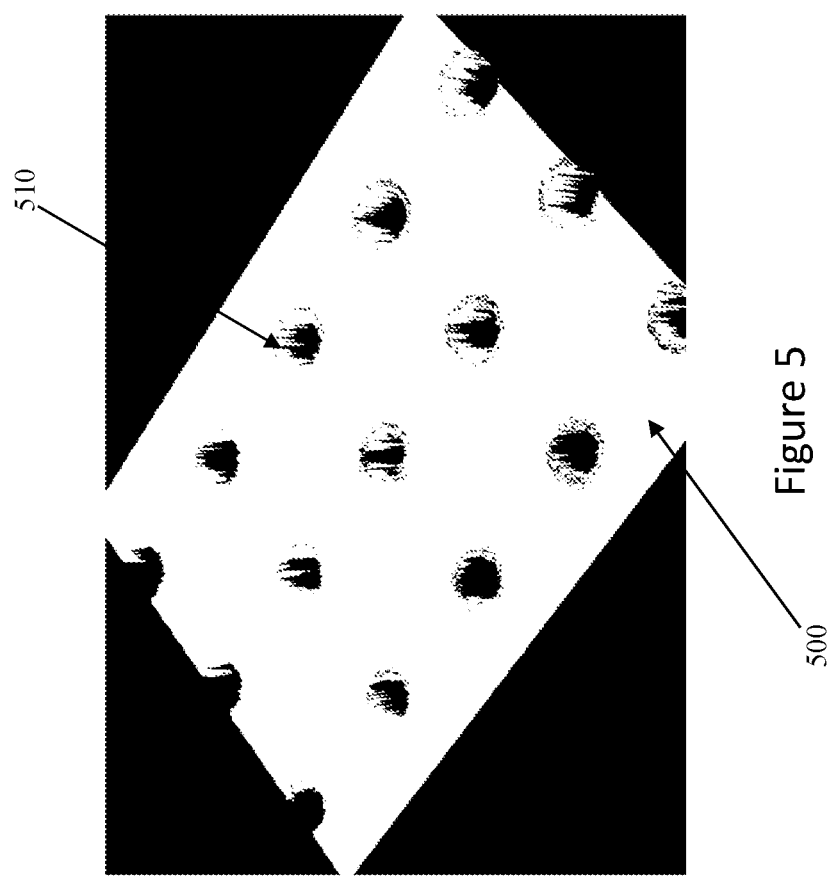
FIG. 5 is a 3D optical profiler view of holes drilled by ultrafast laser machining.

The manufacturing method as described above requires micro-machining of holes through the first filter layer (long-pass filter). This has been demonstrated by ultrafast laser machining, as shown in FIG. 5. FIG. 5 shown as example of machining of holes for multiple micro-filters being prepared on one substrate. As discussed above the diameter of each hole 510 is around 4 µm to match the DCF core diameter for the probe. Once the micro-filter structure is applied to the substrate this can be separated (for example diced or core drilled) into individual micro-filters for attaching to DCF optical fibre tips. This can have significant manufacturing efficiency advantages (time, cost, quality control etc.) over prior art devices where filters were individually manufactured (for example Komachi discussed above).

Embodiments can also utilise state-of-the-art thin film filter technology to deposit the second filter (short pass or band pass).

Advantages of this filter manufacture methodology can include (a) reducing cost and complexity by using a single optical fibre, (b) reducing the cost of filter production through chip-based manufacturing, (c) simplifying filter alignment with the concentric filter structure that requires a single alignment with the inner core of the DCF, and (d) further miniaturising the probe below 500 µm diameter.

Further advantages of this approach are that a SERS substrate can be integrated onto the outer surface of the filter assembly, or alternatively, an angled planar or concave mirror can be used to direct excitation light to an off-axis target and return a portion of the resulting scattered light back into the DCF for analysis.

Surface-enhanced Raman scattering (SERS) has emerged as an important analytical technique with a wide range of applications. However, despite the high level of research interest, the technique remains largely confined to specialist research laboratories. This is in contrast to normal Raman scattering (NRS), which has successfully made the transition to industrial practice. The following section discusses the inventors' developments in surface chemistry for SERS sensing which can be used in conjunction with the above described optical fibre microprobe.

Surface-enhanced Raman scattering (SERS) has been identified as a technique which has great promise for biosensing and diagnostic applications. It has high sensitivity and has achieved single molecule detection. Under standard conditions, the sensitivity of SERS is competitive with fluorescence sensing techniques, but the information-rich spectrum provides a "fingerprint" confirmation of the target analyte while avoiding the need to introduce a fluorescent label, thus reducing the complexity of the chemistry and the potential for interference. However, there remain several technical barriers to its widespread adoption:

1. Some existing SERS sensing methods (e.g. JP2005524849A, US20060014172A1) require functionalisation of both a macroscopic surface and a nanoparticle probe surface with separate recognition molecules, which are most commonly "sandwich" antibodies. This approach immobilises the target analyte and the nanoparticles that produce the SERS spectrum at a known location on the surface where the measurement can take place. The requirement for multiple functionalisations increases (a) the difficulty in targeting a wide range of analytes, especially small molecules, (b) the potential for interference from complex biological matrices, (c) the potential for random orientation of the recognition molecules and the analyte on the capture surface and (d) the effective distance of the analyte from the SERS substrate (the SERS signal drops to approximately 10% of its peak value over the typical 8-11 nm length of an antibody. It should be noted that this drop in SERS signal is even worse in sandwich assays where pairs of antibodies are used, thus doubling the distance to the analyte.

2. In conventional assays this random orientation leads to poor availability of recognition sites giving reductions in sensitivity of up to 2 orders of magnitude. For a label-free SERS method, random orientation of target analyte or of the capture molecules will also result in differences in the microenvironment of the analyte which will strongly influence the reproducibility of the SERS fingerprint. These differences may include differences in distance from the substrate and/or the nanoparticle probe surface, solvent availability, differences in hydrophobicity and in proximity of SERS active features in the analyte to different chemical entities. These effects may be increased if the capture molecule is not present as a monolayer (e.g. physisorbed antibody).

3. The reproducibility of the SERS fingerprint for target analytes has been recognised as a limiting factor. The lack of reproducibility may make identification of the analyte challenging and additionally, there may be difficulties of interpretation due to the presence of matrix in biological samples. Quantification may also be challenging as the correlation of spectral intensity with concentration may vary with the homogeneity of the SERS substrate. Research has shown improvement in the reproducibility of SERS spectra when analytes are in a uniform orientation, and has been confirmed by measuring a compound which was amenable to alignment on a SERS substrate by adjustment of the pH. It is therefore desirable to achieve homogeneity and alignment when producing the SERS substrate.

4. Some SERS "sandwich assays" may employ a SERS-active tag to improve the sensitivity and reproducibility. However, these tags require additional chemical functionalisations, and do not provide the direct confirmation of analyte concentration that can be obtained from the intrinsic SERS spectrum.

5. In addition, the use of colloidal nanoparticles raises the challenge of stabilising the nanoparticles in suspension, particularly during transport and storage, but also during interactions with complex biological substrates. Nanoparticles also present challenges with controlling the distance from the analyte when using capture molecules and linker chemistries. This may reduce the SERS enhancement or lead to variability in intensity (see item 2 above).

6. Other SERS assays have functionalised surfaces with semi-selective partition layers e.g. mixed alkane-thiol self-assembled monolayers. These approaches are difficult to generalise and essentially require unique chemistries for each specific target. They are also susceptible to unpredictable interferences in complex biological matrices.

7. SERS substrates can also be formed via a range of physical vapour deposition techniques. Metal surfaces in general, and silver in particular, are prone to atmospheric contamination by hydrocarbon species when exposed to air.

In contrast, the inventors have developed a technique for on-demand photochemical deposition of SERS nanoparticles which avoids issues with nanoparticle stability and surface contamination, and appears to be robust for a wide range of surface chemistries.

One major obstacle to the uptake has been the challenge of fabricating stable, reproducible and sensitive SERS substrates that are low cost and sufficiently robust for use in the production line, clinic or field. Optical fibre SERS sensors previously used also have drawbacks including interference due to ambient light, limited stability of the sensor, background absorption, fluorescence and Raman scattering from the fibre itself. Some of these problems can be alleviated in embodiments of the present probe tip with an SERS substrate applied, this is partly based on the advantage that a single fibre carries both the excitation light and backscattered signal (within the core and multimode cladding respectively) and due to the integrated filtering.

The SERS substrate should be reasonably transparent, as scattered light arising at the sampling interface should be able to pass back through the substrate to be captured by the optical fibre. It has been observed that higher SERS intensities can be obtained for reverse-side excitation than for front-side measurements under appropriate conditions.

In some embodiments of the probe tip the SERS substrate is applied to the probe tip with the integrated filter using a photochemical deposition method. In this method the probe tip is inserted into a photochemical growth solution, and laser irradiation applied via the DCF core for a period of time to stimulate photochemical deposition on the probe tip from the growth solution.

In embodiments of this on-demand technique, photo-deposition occurs in the fluid phase and thus avoids air contamination associated with vacuum deposition techniques. SERS measurement in the fluid phase can also have advantages in the fluid removing heat and preventing thermal degradation of the sample. This can allow shorter measurement times at higher laser excitation power. Previous disclosures of SERS sensing with photochemical deposition have relied on complex surface chemistries that mitigated these advantages.

In some embodiments the SERS substrate is formed on top of a target analyte capture layer. The primary innovation of the proposed method is based on the discovery that photochemical deposition can be used to produce the SERS-active film over the top of the target analyte, after the analyte capture and partitioning processes have been completed. When combined with an appropriate analyte capture and separation chemistry, as described in the embodiment illustrated in FIG. 7 this approach resolves all of the issues identified above.

Figure 7:
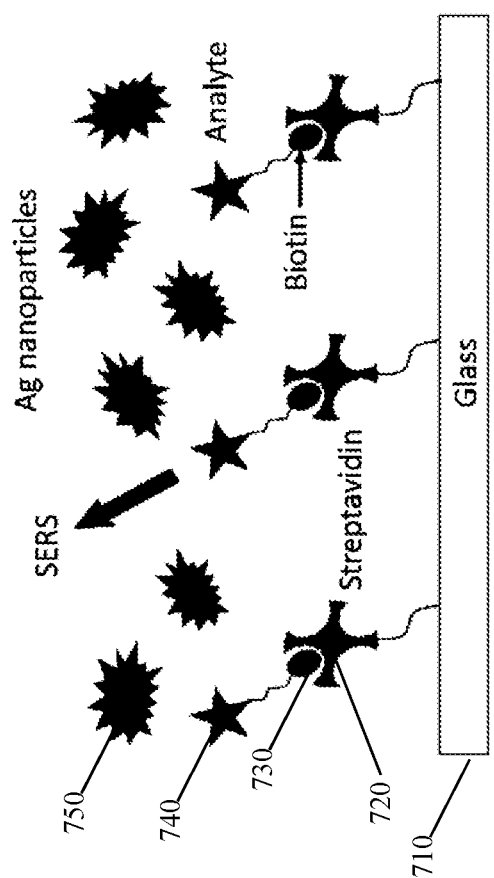
FIG. 7 is a schematic illustration of some components of one embodiment of an SERS substrate deposition method.
Figure 8:
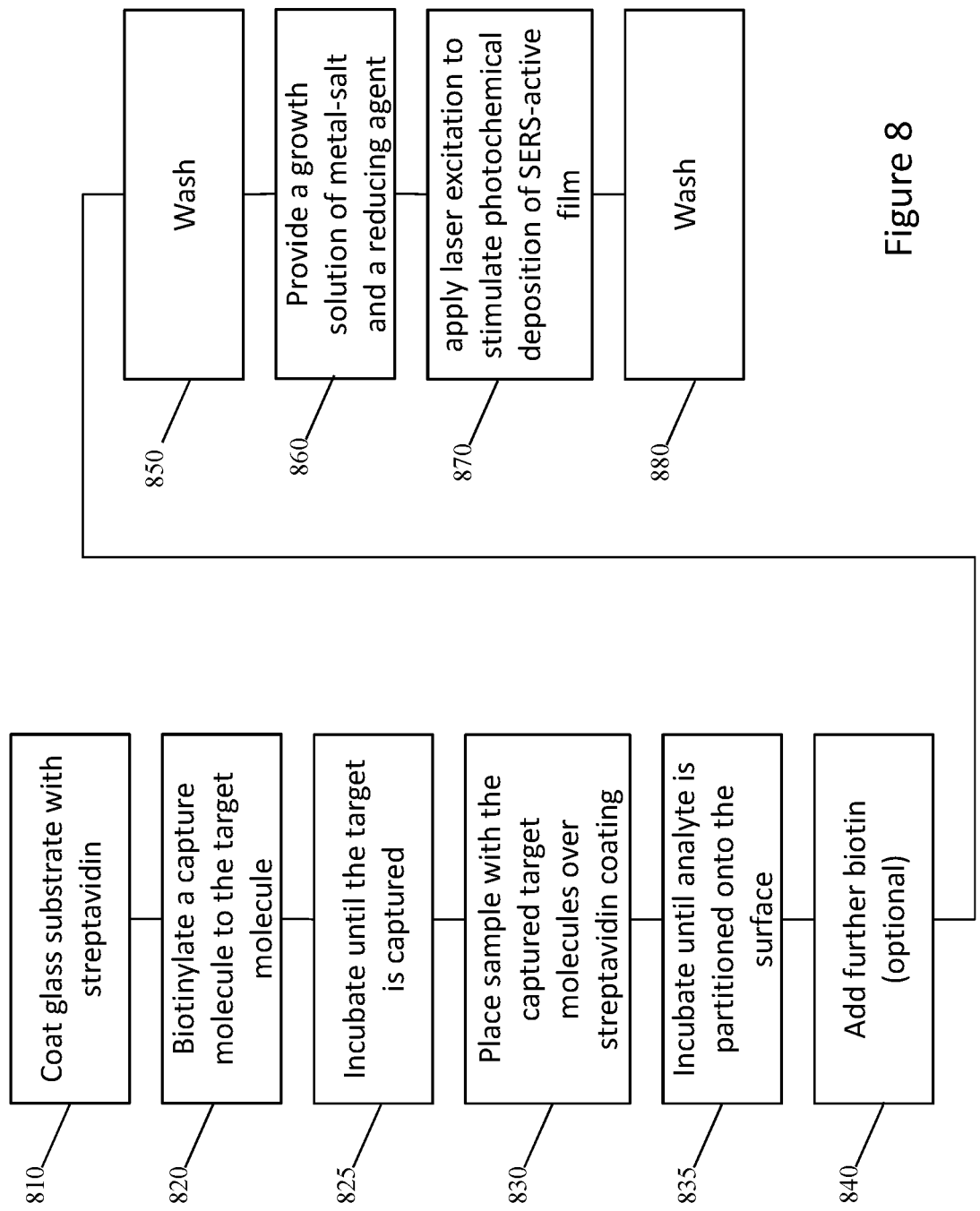
FIG. 8 is a flowchart of an embodiment of a method for preparing an SERS substrate.

FIG. 7 schematically illustrates some of the main components of this embodiment, and FIG. 8 is a corresponding flow chart of the process. In this embodiment biotinylated antibodies capture the target analyte in solution and are then partitioned out of the matrix onto a streptavidin-coated surface via the strong streptavidin-biotin interaction. A SERS-active film is then deposited over the top of the surface and in close proximity to the target compound by means of a photo-chemical reaction.

In the embodiment of FIGS. 7 and 8, in step 810 a glass substrate 710 (for example the end of a probe tip or surface of a filter attached to a probe tip) is coated with a monolayer of streptavidin 720. This can be performed using a range of well-established standard approaches. Next 820 a capture molecule 730 appropriate to the target molecule is biotinylated, again using a range of well-established approaches. The biotinylated capture molecule 730 is then added to a defined quantity of a sample containing the target analyte 740 and is incubated 825 until the target has been captured. These steps may be performed as part of the process of forming the SERS preparation of the microprobe, but may also be performed separately and the biotinylated analyte 740 provided pre-prepared. In some embodiments the target molecules are introduced to biotinylated capture molecules and incubated. After incubation for a specific period and at a controlled temperature to allow binding of the target molecules to biotinylated capture molecules, the combined solution can be introduced to the streptavidin coated optical fibre surface.

In step 830 the sample with captured analyte 740 is then placed over the streptavidin-coated surface 710 and incubated 835 until the biotinylated analyte has been partitioned onto the surface by the strong biotin-streptavidin interaction.

At this stage the analyst may optionally choose to add further biotin 840 to act as an internal standard. Robust, well characterised binding of biotin to streptavidin can ensure the target analyte molecules are partitioned onto the optical fibre surface. Any unbound sites on the streptavidin can then be saturated with pure biotin or another biotinylated tag that can act as an internal standard for chemometric analysis (optional). The sample is then thoroughly washed.

After thorough washing 850, the sample is then replaced by a solution of metal-salt and a reducing agent 860 (e.g. silver nitrate and sodium citrate) so that a SERS-active film 750 can be photo-deposited 870 over the top of the target analyte. The photo-deposition may be performed as explained in further detail below with reference to FIG. 6, or using conventional techniques. This is followed 880 by further washing finally immersion in pure water.

In some embodiments, the target analyte-coated optical fibre tip is immersed in a growth solution of silver salt (e.g. silver nitrate and sodium citrate). Silver nanoparticles are then deposited over the top of the target analyte layer by means of a photochemical reduction. Sample is then thoroughly washed.

Following deposition of the nanoparticles over the analyte, the surface-enhanced Raman scattered signal from the target molecules is measured with the surface immersed in pure water.

It will be recognised by those skilled in the art that this approach can be extended to types of surfaces other than glass (e.g. polymer surfaces), can be parallelised through the use of arrays or multiple functionalised capture molecules, can use a wide range of capture chemistries (e.g. FAB fragments, nano FABs, aptamers, etc) and could make use of other robust antibody-antigen pairs to partition the target onto the surface (e.g. digoxigenin conjugations).

In embodiments SERS spectra are acquired by coupling a laser to the distal end of the optical fibre from that on which the analyte has been immobilised. SERS measurements through an optical fibre probe provide averaging over a wider measurement area than the spot size of a standard Raman microscope objective. For example, the core area of a DCF for visible light (e.g. 514.5 nm excitation) is approximately equivalent to 12 measurements taken through a 50× objective.

The proposed method simplifies the chemistry by using robust surface functionalisation and target recognition chemistries on the macroscopic surface, thus reducing the potential for chemical interference and variable surface orientation. The initial analyte capture is performed in the liquid phase where diffusional behaviour is more easily characterised and surface effects are irrelevant. The use of stiff linker chemistries is preferred as that can help to reduce the molecular motion of the analyte and produce a reproducible orientation for subsequent detection.

Photochemical deposition can be performed as part of a kit-based assay using a disposable optical fibre probe, Raman microscope, or Raman plate reader. As one embodiment, the optical fibre probe offers the advantage of signal averaging over an extended measurement region for improved quantitation of analyte concentration. Alternatively, the assay could be integrated into a microfluidic device using conventional bulk sampling optics or microscope optics and averaging over multiple measurement positions if required.

Figure 6:
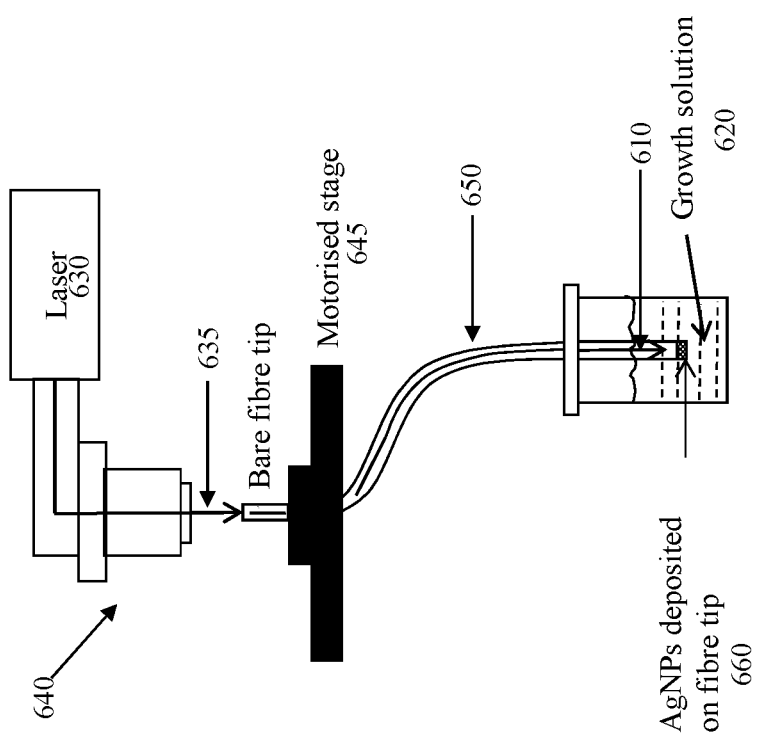
FIG. 6 represents an example of photochemical deposition of AgNPs.

An example of a photochemical deposition process is illustrated in FIG. 6, for applying a SERS substrate of silver nanoparticles (AgNPs) 750 to an optical fibre tip. The probe tip 610 is inserted into the growth solution 620. In this example the growth solution is an aqueous solution of silver nitrate and tri sodium citrate, 1:1 ratio, 1 mM concentration. FIG. 6 illustrates a Raman microscope arrangement for coupling the laser excitation 635 from the laser source 630 to the DCF probe 650 via a Raman microscope. In this example the bare fibre tip is aligned with the laser excitation 635 using the motorised stage 645 of the microscope. However, this could equally be a laser system fitted with an industry standard optical fibre coupler. The laser excitation may also be provided using a conventional Raman spectroscopy source.

In this example the length of the DCF probe 650 used for AgNPs deposition is 5 m. The laser wavelength is 514.5 nm and laser power 6.4 mW. The probe tip is irradiated for 3.5 minutes. During this time silver nanoparticles are deposited on the fibre tip though photochemical deposition to provide the SERS substrate. The length of processing time can be varied to increase or decrease the density of the SERS substrate.

It should be noted that the deposition does not necessarily occur over the entire probe tip. The extent of coverage will depend on the thickness of the filter. However, the SERS deposition centres on the region illuminated by the laser beam. In principle, for Raman/SERS measurements with excitation wavelengths less than about 500 nm, we can use the same laser to perform the photochemical deposition. The integrated filter ensures complete alignment of the substrate with the optical axis of the fibre for optimal excitation and signal collection. The size of the substrate can be controlled by means of the thickness of the filter. In general, the thicker the filter, the bigger the substrate, due to the expansion of the laser beam as it leaves the core of the fibre. Larger substrate size may have advantages for:

(a) spatially averaging the SERS signal to achieve improved repeatability and quantitation,
(b) allowing an increase in SERS signal by increasing the laser power while maintaining a safe power per unit area of substrate to avoid thermal damage, and
(c) optimizing the size of the substrate for efficient signal collection (many prior art substrates are much larger than the region that can reasonably be measured, thus providing inefficient use of materials).

This example uses chemicals and laser irradiation with specifications commonly used for deposition of AgNPs. The method is robust and effective under a reasonably broad range of processing parameters. A similar approach can be used to deposit gold nanoparticles. Many variations of photochemical deposition processes are available, and appropriate materials to develop a SERS substrate may be chosen based on the intended purpose of the probe.

It should be appreciated that a further advantage of this arrangement is that the fibre tip could be prepared immediately prior to use (using the same laser to activate the SERS tip and then perform the SERS experiment). Alternatively, the prepared SERS probe tip could be stored and transported in the liquid environment to reduce contamination from exposure to hydrocarbons in the air. Contamination of SERS substrates is known problem. The ability for embodiments of the present probe to use this simple method to apply an SERS substrate as needed, and only requiring a container of growth solution in addition to standard spectroscopy equipment has significant convenience advantages for researchers and clinicians, and may facilitate a dramatic increase in uptake of SERS in a range of areas, including medical diagnostics.

Embodiments of the probes as discussed above provide significant advantages over current Raman spectroscopy probe technology. A DCF coupler as shown in FIG. 2 used together with the integrated filtering at the tip of the DCF Port S has an advantage of avoiding bulky free-space optics. The microprobe can effectively reduce the silica Raman background resulting in increased signal to background ratio, enabling detection of chemicals of interest for biological, environmental or industrial analysis.

The smaller diameter of the microprobe compared to prior art can enable it to be used in a minimally invasive approach for real-time sensing in point-of-care diagnostics or process monitoring. Prior to the inventors' developments, the smallest probe described in the literature had an outer diameter of 600 μm.

Embodiments of the disclosed probes have three main advantages compared to competing products:
more compact as it integrates the Raman filters for background removal.
more robust as it reduces the need for alignment of bulky free-space optics.
more versatile as it supports SERS operation if needed.

These advantages provide a cost benefit that may, for example, allow a disposable device that avoids the need for repeated sterilization. The compact design makes the probe more flexible and therefore less invasive. For example, the small diameter of the probe could allow it to be inserted virtually painlessly via a catheter or a hypodermic needle for in vivo diagnostic purposes. Greater robustness reduces the level of skill required from the operator.

These probes offer significant opportunities for researchers and clinicians alike, for example:

1. Raman probes are already available for cancer diagnostics, but are relatively expensive and bulky. Embodiments of the probes herein described are smaller and potentially more economical for diagnostic use.

2. Use of these probes may enable label free and minimally invasive sensing of biomolecules.

3. These probes could lead to wearable sensing probes for point-of-care diagnostics.

4. These probes may feasibly be used economically for quality control and detection of impurities or contamination in food/chemicals; or detection of hazardous components in the environment.

There is a need for continuous or real-time diagnostics in various medical fields e.g. detecting tumour margins during surgery. Applications of Raman scattering in medical diagnostics have been demonstrated, but these methods are taking time to win acceptance as diagnostic standards. Inhibitors to increased use of diagnostic Raman scattering may include probe cost, sterilisation requirements and the precision optics compromising device robustness. Using the probe configuration and manufacturing methodologies disclosed enable compact probes. These probes may be more affordable than current technologies, leading potentially to use as a disposable component avoiding the need for sterilisation protocols. The probes may also be more robust and/or usable in a wider range of diagnostic applications than currently available probes. Availability of more compact, affordable and robust probes may promote more widespread adoption of this sensing technology in medical diagnostics. For example, affordable disposable probes will reduce the need for repeated sterilisation, while increased robustness will reduce the skill level required from the operator.

It will be understood to persons skilled in the art of the invention that many modifications may be made without departing from the spirit and scope of the invention.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or any other country.

The invention claimed is:

1. A spectroscopy probe for a Raman spectroscopy system, the probe comprising:
    a double-clad optical fibre probe tip, the double-clad optical fibre (DCF) having a single mode core, multimode inner cladding, and outer cladding; and
    a micro-filter fixed to the distal end of the optical fibre probe tip,
    the micro-filter comprising:
    a short pass or band pass filter configured to align with the DCF core to filter silica Raman background generated by laser excitation in the single mode core, and
    a long pass filter configured to suppress Rayleigh scattering from the sample while allowing Raman scattered wavelengths to be transmitted through the inner cladding.

2. A spectroscopy probe as claimed in claim 1 wherein the micro-filter is substantially planar and wherein the long pass filter surrounds the short pass or band pass filter aligned substantially in the same plane and the outer diameter of the filter at least matches the diameter of the inner cladding of the double-clad optical fibre.

3. A spectroscopy probe as claimed in claim 1 wherein the micro-filter further comprises a surface-enhanced Raman scattering (SERS) substrate.

4. A spectroscopy probe as claimed in claim 3 wherein the SERS substrate is applied using a photo chemical deposition technique.

5. A spectroscopy probe as claimed in claim 1 wherein a SERS substrate is applied by:
    inserting the probe tip into a photochemical growth solution; and
    applying laser irradiation via the DCF core for a period of time to stimulate photochemical deposition on the probe tip from the growth solution.

6. A spectroscopy probe as claimed in claim 1 wherein the micro-filter is attached directly to the end of the optical fibre using UV light curable adhesive.

7. A spectroscopy probe as claimed in claim 1 further comprising a double-clad optical fibre coupler configured to couple a double-clad optical fibre and a multimode fibre, wherein a distal end of the double-clad optical fibre forms the probe tip and a proximal end of the double-clad optical fibre is configured for connection to an excitation output of the Raman spectroscopy system, to in use convey excitation wavelengths to the probe tip via the core of the double-clad optical fibre; and a proximal end of the multimode fibre is configured for connection to a detector input of the Raman spectroscopy system, such that Raman scattered wavelengths transmitted through the inner cladding of the double-clad optical fibre in response to excitation are coupled to the multimode fibre for reception by the detector.

8. A method of fabricating a Raman spectroscopy micro-filter for a Raman spectroscopy probe, the method comprising the steps of:
    depositing on an optically transparent substrate a thin film of material having long pass filter properties, to provide a long pass filter layer;
    removing a section of the long pass filter layer to leave a hole in the long pass filter layer to align with an optical fibre inner core;
    applying a layer of resist coating, whereby the resist coating fills the hole and provides a layer over the long pass filter layer, the resist coating being removable through developing after exposure to UV light;
    illuminating the glass substrate with UV light whereby the long pass filter layer blocks the UV light and the resist filling and above the hole is exposed to UV radiation;
    developing to remove the UV exposed resist, to leave empty the hole extending through the long pass filter layer and resist layer;
    depositing a thin film of material having short or band pass properties to provide at least a layer of short or band pass filter material on the substrate inside the hole; and
    removing the resist layer and any band pass filter material on top of the resist layer to provide a substantially planar filter surface, the resulting micro-filter comprising a filter layer having a short or band pass filter surrounded by a long pass filter supported on a substrate.

9. A method of fabricating a Raman spectroscopy micro-filter for a Raman spectroscopy probe, the method comprising the steps of:
    depositing on a first side of an optically transparent substrate a thin film of material having long pass filter properties, to provide a long pass filter layer;
    depositing a thin film of material having short pass filter properties, on a second side of the substrate to provide a short pass filter layer;

removing a ring-shaped section of the short or band pass filter layer to leave a central circular portion and an annular outer ring portion;

removing a section of the long pass filter layer to leave a hole in the long pass filter layer aligned with the central circular portion of the short pass filter; and attaching a further substrate to the long pass filter layer, to provide a resulting micro-filter comprising annular long pass and short pass filters, with a short or band pass filter surrounded by a long pass filter supported on a substrate.

10. A method as claimed in claim 8 wherein the step of removing a section of the long pass filter layer comprises any one or more of: drilling, laser drilling, micromachining or etching.

11. A method as claimed in claim 8 wherein the method is used to produce a plurality of micro-filters on one substrate and the step of removing a section of the long pass filter layer comprises removing a plurality of sections of the long pass filter layer, to provide one hole for each micro-filter.

12. A method as claimed in claim 11 further comprising the further step of separating the individual filters.

13. A method as claimed in claim 8 wherein the substrate is formed of any one or combination of, glass or fused silica.

14. A method as claimed in claim 8 further comprising the step of attaching the micro-filter to a double-clad optical fibre probe tip, with the short pass filter aligned with the optical fibre core.

15. A method as claimed in claim 14 wherein the micro-filter is attached to the probe tip using UV cured adhesive.

16. A method as claimed in claim 14 further comprising applying a surface enhanced Raman scattering (SERS) substrate to the micro-filter at the probe tip.

17. A method as claimed in claim 16 wherein the SERS substrate is formed on top of a target analyte capture layer.

18. A method as claimed in claim 17 wherein the target analyte capture layer is formed by:

coating the probe tip surface with a layer of streptavidin;

providing biotinylated analyte to the streptavidin substrate; and incubating to partition the biotinylated analyte onto the surface by biotin-streptavidin interaction to form the target analyte capture layer.

19. A method as claimed in claim 16 wherein applying a SERS substrate comprises the steps of:

inserting the probe tip into a photochemical growth solution; and applying laser irradiation via the DCF core for a period of time to stimulate photochemical deposition on the probe tip from the growth solution.

20. A method as claimed in claim 19 wherein the photochemical growth solution is an aqueous solution of silver nitrate and trisodium citrate, for deposition of silver nanoparticles in response to irradiation.

* * * * *